United States Patent
Shirono (10) Patent No.: US 10,980,495 B2
(45) Date of Patent: Apr. 20, 2021

(54) CT APPARATUS, CT IMAGING METHOD, AND STORAGE MEDIUM

(71) Applicant: CANON KABUSHIKI KAISHA, Tokyo (JP)

(72) Inventor: Jumpei Shirono, Yokohama (JP)

(73) Assignee: CANON KABUSHIKI KAISHA, Tokyo (JP)

(*) Notice: Subject to any disclaimer, the term of this patent is extended or adjusted under 35 U.S.C. 154(b) by 202 days.

(21) Appl. No.: 16/011,933

(22) Filed: Jun. 19, 2018

(65) Prior Publication Data
US 2018/0296170 A1 Oct. 18, 2018

Related U.S. Application Data

(63) Continuation of application No. PCT/JP2016/082422, filed on Nov. 1, 2016.

(30) Foreign Application Priority Data

Dec. 28, 2015 (JP) .............................. JP2015-257326

(51) Int. Cl.
*A61B 6/00* (2006.01)
*A61B 6/03* (2006.01)
(Continued)

(52) U.S. Cl.
CPC ............ *A61B 6/032* (2013.01); *A61B 6/4241* (2013.01); *A61B 6/482* (2013.01); *A61B 6/5205* (2013.01);
(Continued)

(58) Field of Classification Search
CPC ....... A61B 6/032; A61B 6/4241; A61B 6/481; A61B 6/482; A61B 6/5205; A61B 6/5217;
(Continued)

(56) References Cited

U.S. PATENT DOCUMENTS

| 8,243,874 B2 * | 8/2012 | Carmi ................... G01T 1/1644 378/5 |
| 10,083,526 B2 * | 9/2018 | Hagiwara ............. G06T 7/0016 |

(Continued)

FOREIGN PATENT DOCUMENTS

| JP | 2014239840 A | 12/2014 |
| WO | 2009131109 A1 | 10/2009 |
| WO | 2015046668 A1 | 4/2015 |

OTHER PUBLICATIONS

Ruoqiao Zhang, Jean-Baptiste Thibault, Charles A. Bouman, et al.: "Model-Based Iterative Reconstruction for Dual-Energy X-Ray CT Using a Joint Quadratic Likelihood Model"; IEEE Trans. on Medical Imaging; vol. 33, No. 1 (Jan. 2014), pp. 117-134.

*Primary Examiner* — Irakli Kiknadze
(74) *Attorney, Agent, or Firm* — Carter, DeLuca & Farrell LLP (57) ABSTRACT

Information of constituent substances of an object is reconstructed with high accuracy without being influenced by a decrease in measurement accuracy even if measurement in which a tube voltage is changed is not performed. A CT apparatus includes: a detection unit configured to obtain measurement information based on a detection result of radiation irradiated based on a constant tube voltage; an obtaining unit configured to obtain second measurement information of the radiation based on a moment of the measurement information obtained by detecting the radiation a plurality of times; a classification unit configured to classify an object into a plurality of substances; and a reconstruction unit configured to reconstruct the information of the constituent substances of the object based on the second information.

14 Claims, 5 Drawing Sheets

(51) Int. Cl.
*G06T 11/00* (2006.01)
*G01N 23/046* (2018.01)
*G01N 23/04* (2018.01)

(52) U.S. Cl.
CPC ........... *A61B 6/5217* (2013.01); *G01N 23/04* (2013.01); *G01N 23/046* (2013.01); *G06T 11/006* (2013.01); *A61B 6/481* (2013.01); *G01N 2223/045* (2013.01); *G06T 2207/10081* (2013.01); *G06T 2207/20212* (2013.01); *G06T 2211/408* (2013.01)

(58) Field of Classification Search
CPC ....... A61B 6/037; A61B 6/5235; A61B 6/405; A61B 6/027; A61B 6/4035; A61B 6/542; A61B 6/00; A61B 6/4233; A61B 6/4275; A61B 6/466; A61B 6/541; A61B 6/4028; A61B 6/0457; A61B 6/14; A61B 6/4441; A61B 6/469; A61B 6/484; A61B 6/5223; A61B 6/583; A61B 6/503; A61B 6/5264; A61B 6/02; A61B 6/4085; A61B 6/4291; A61B 6/502; A61B 6/505; A61B 6/4266; A61B 5/055; A61B 2576/00; A61B 5/0205; A61B 5/4504; A61B 5/7264; A61B 5/7275; A61B 5/743; A61B 6/0407; A61B 6/0487; A61B 6/06; A61B 6/40; A61B 6/465; A61B 6/488; A61B 6/54; A61B 6/585; A61B 5/0035; A61B 6/5288; A61B 6/543; A61B 6/563; A61B 34/10; A61B 6/463; A61B 2034/101; A61B 5/004; A61B 5/02007; A61B 5/026; A61B 5/029; A61B 5/1079; A61B 6/12; A61B 6/461; G01N 2223/045; G01N 23/04; G01N 23/046; G01N 2232/0563; G01N 2223/423; G01N 23/20091; G06T 11/006; G06T 2207/10081; G06T 2207/20212; G06T 2211/408; G06T 11/003; G06T 11/008; G06T 2207/20021; G06T 2207/30028; G06T 2207/30048; G06T 2211/412; G06T 7/0012; G06T 19/006; G06T 2211/404; G06T 2207/20036; G06T 2207/20221; G06T 7/0016; G06T 2211/424; G06T 5/002; G06T 7/215; G06T 7/38; G06T 7/97; G06T 11/005; G06T 1/00; G06T 2207/10072; G06K 9/00; G01T 1/2985; G01T 1/1644; G01T 1/17; G01T 1/171; G01T 1/2002; G01T 1/247; G01T 1/249; G01T 1/1615; G01T 1/2018; G01T 1/2006; G01T 1/248; G01T 1/29; G01T 1/2914; G01T 1/2928; G01T 1/161; H01L 27/144; H01L 31/02019; H01L 31/107; G01B 15/00; A61N 2005/1072; A61N 5/1048; A61N 5/1049; H04N 5/32; H04N 5/202; G16H 40/40; G16H 40/63; G16H 50/30; H01J 35/00; H01J 35/147; H05G 1/52; H05G 1/62; H05G 1/265; H05G 1/34
USPC .......................... 378/4, 19, 62, 98.8; 250/580
See application file for complete search history.

(56) References Cited

U.S. PATENT DOCUMENTS

| | | | |
|---|---|---|---|
| 2004/0066978 A1* | 4/2004 | Nanbu | G06T 5/002 382/261 |
| 2009/0008581 A1* | 1/2009 | Fujiwara | G01N 23/046 250/580 |
| 2010/0020922 A1* | 1/2010 | Carmi | G01T 1/2985 378/19 |
| 2013/0251096 A1* | 9/2013 | Hiraoka | A61B 5/7264 378/8 |

* cited by examiner

CT APPARATUS, CT IMAGING METHOD, AND STORAGE MEDIUM

CROSS-REFERENCE TO RELATED APPLICATIONS

This application is a Continuation of International Patent Application No. PCT/JP2016/082422, filed Nov. 1, 2016, which claims the benefit of Japanese Patent Application No. 2015-257326, filed Dec. 28, 2015, both of which are hereby incorporated by reference herein in their entirety.

BACKGROUND OF THE INVENTION

Field of the Invention

The present invention relates to a CT apparatus, a CT imaging method, and a storage medium.

Background Art

A CT apparatus is an apparatus that can obtain a spatial distribution of linear attenuation coefficients or the like of an object by measuring, at various angles, X rays that transmit through an object while an X ray source and a detection unit are rotated centered about the object, and reconstructing the obtained information. With a CT apparatus, the linear attenuation coefficients are obtained as pixel values in units of Hounsfield units in which water is set to 0 and air is set to −1000, or in other words, CT values, for example.

However, when only CT values are used, a case can occur in which substances constituting the object cannot be separated, such as a case in which it is not possible to tell whether a substance is bone or soft tissue. Under these circumstances, a Dual Energy CT apparatus has been developed in recent years. With a Dual Energy CT apparatus, two instances of measurement are performed while changing the spectral distribution of the X rays, and the separation of the substances is performed using the fact that the energy dependency of the mass attenuation coefficient differs according to the substance.

For example, NPTL 1 discloses a method in which water and iodine are envisioned as substances constituting an object, and by performing measurement at a low tube voltage and at a high tube voltage and performing reconstruction processing, the densities of the water and the iodine can be obtained.

However, in the case of performing measurement at several different tube voltages as disclosed in NPTL 1, there has been a problem in that a motion artifact caused by the object moving while the tube voltage is being changed occurs, and the measurement accuracy decreases.

CITATION LIST

Non Patent Literature

NPTL 1: Ruoqiao Zhang, Jean-Baptiste Thibault, Charles A. Bouman, et al. "Model-Based Iterative Reconstruction for Dual-Energy X-Ray CT Using a Joint Quadratic Likelihood Model", IEEE Trans. on Medical Imaging 33 (2014) 117-134.

SUMMARY OF THE INVENTION

In light of the foregoing problem, the present invention provides a CT apparatus that can reconstruct, with high accuracy, information of constituent substances of an object without being influenced by a decrease in measurement accuracy even if measurement in which a tube voltage is changed is not performed.

A CT apparatus according to one aspect of the present invention includes: a detection unit configured to obtain measurement information based on a detection result of radiation irradiated based on a constant tube voltage; an obtaining unit configured to obtain second measurement information of the radiation based on a moment of the measurement information obtained by detecting the radiation a plurality of times; a classification unit configured to classify an object into a plurality of constituent substances; and a reconstruction unit configured to reconstruct information of the constituent substances of the object based on the second measurement information.

Further features of the present invention will become apparent from the following description of exemplary embodiments with reference to the attached drawings.

DESCRIPTION OF THE EMBODIMENTS

DESCRIPTION OF THE EMBODIMENTS

Hereinafter, embodiments of the present invention will be described illustratively and in detail with reference to FIGS. 1 to 5. Note that the constituent elements described in the embodiment are merely examples, the technical scope of the present invention is established by the claims, and there is no limitation to the following individual embodiments.

Figure 1:
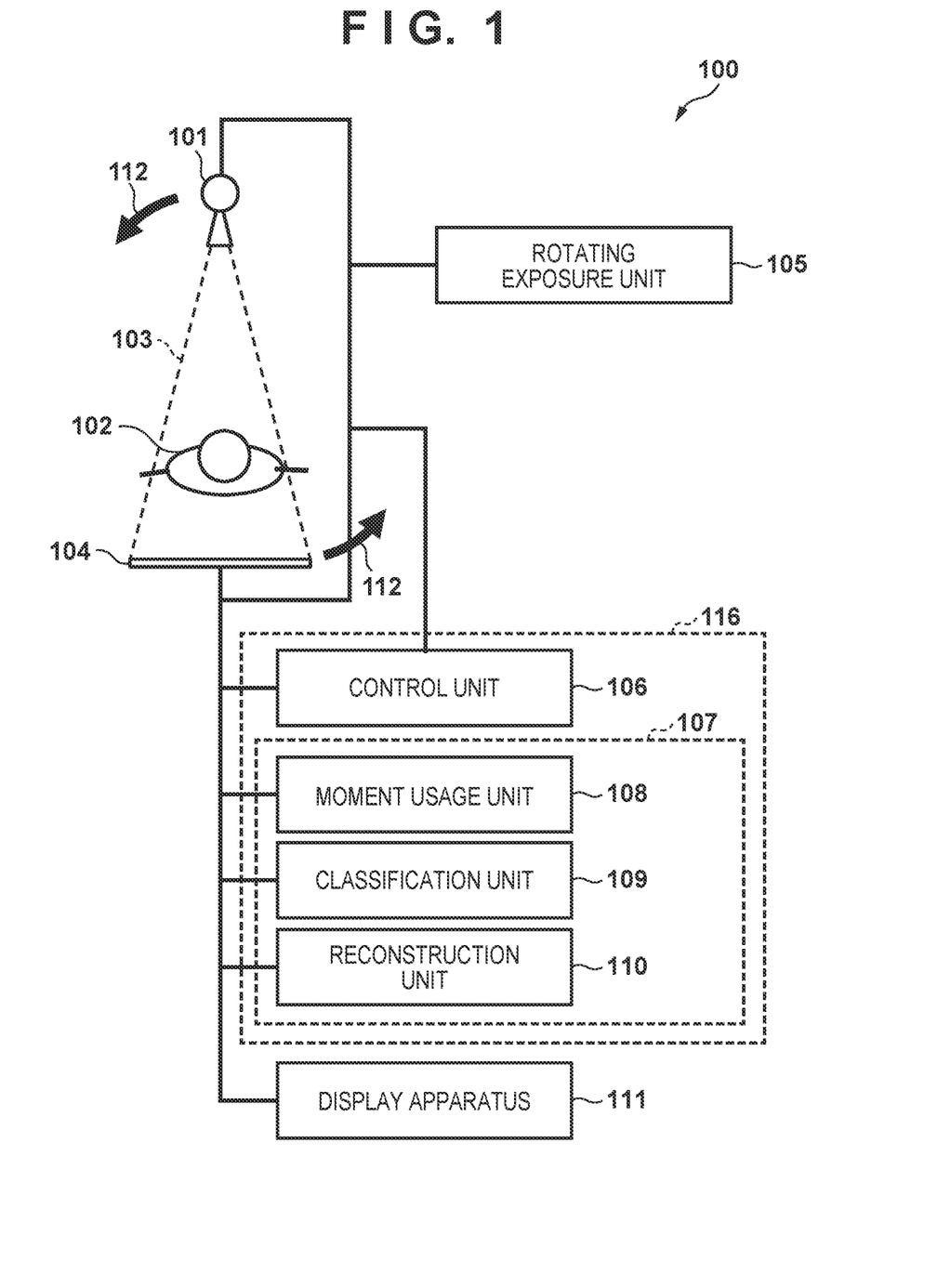
FIG. 1 is a diagram showing an exemplary configuration of a CT apparatus according to an embodiment.

FIG. 1 is a diagram showing an exemplary configuration of a CT apparatus 100 of an embodiment. As shown in FIG. 1, the CT apparatus 100 includes a radiation generating apparatus 101, a radiation detection apparatus 104, a rotating exposure unit 105 that drives the radiation generating apparatus 101 and the radiation detection apparatus 104 so as to rotate in a state of opposing each other, and an information processing apparatus 116. Note that this configuration is also called a CT imaging system. The information processing apparatus 116 includes a control unit 106 that controls the operations of the radiation generating apparatus 101 that irradiates radiation, the radiation detection apparatus 104, and the rotating exposure unit 105, and a data processing unit 107 that processes data detected by the radiation detection apparatus 104. Also, for example, a display apparatus 111 constituted by a liquid crystal display, a CRT, or the like is connected to the information processing apparatus 116, and the display apparatus 111 displays the processing result of the data processing unit 107. The control unit 106 functions also as a display control unit that controls display of the display apparatus 111.

The rotating exposure unit 105 is a drive unit that synchronizes the radiation generating apparatus 101 and the radiation detection apparatus 104 and then performs driving so as rotate centered about the object 102, based on the control performed by the control unit 106. Arrow 112 indicates the rotation direction. Note that the rotation center need not be centered about the object 102, but rotation needs to be performed in a state in which the radiation generating apparatus 101 and the radiation detection apparatus 104 oppose each other on opposite sides of the object 102. In FIG. 1, the arrow 112 indicating the rotation direction is the rotation direction about a slice cross-section with respect to the object 102, but there is no limitation to this example, and for example, the object 102 may be scanned while the radiation generating apparatus 101 and the radiation detection apparatus 104 rotate in a direction orthogonal to the page surface of FIG. 1.

The control unit 106 functions as an irradiation control unit to cause the radiation generating apparatus 101 to irradiate radiation based on a constant tube voltage. That is, the control unit 106 performs control to apply a set constant tube voltage to the radiation generating apparatus 101, and thus controls the irradiation of the radiation performed by the radiation generating apparatus 101. The radiation generating apparatus 101 outputs the radiation based on the control performed by the control unit 106. Reference numeral 103 schematically indicates the radiation emitted from the radiation generating apparatus 101. The radiation is X rays, α rays, β rays, or γ rays, for example.

The control unit 106 functions as an imaging control unit to control the rotating exposure unit 105 and cause radiation to be irradiated from the radiation generating apparatus 101 based on a constant tube voltage in a state in which the radiation generating apparatus 101 and the radiation detection apparatus 104 are rotated to a predetermined angle, and controls the radiation detection apparatus 104 to cause the detection result of the radiation incident on the radiation detection apparatus 104 to be output each certain period. For example, the control unit 106 controls the radiation generating apparatus 101 so as to irradiate radiation at a constant tube voltage, and can cause the detection result of the radiation incident on the detection units of the radiation detection apparatus 104 to be output as detection data (measurement information) each certain period.

A detection unit of the radiation detection apparatus 104 outputs measurement information that is proportional to the sum of the energies of the radiation that is incident for a certain time period (e.g., a predetermined time period (one frame)). The radiation detection apparatus 104 can obtain measurement information based on the detection result of the radiation irradiated based on the constant tube voltage. Specifically, the radiation detection apparatus 104 includes a detection unit (detection element) that detects radiation that was irradiated based on the constant tube voltage, and the detection unit outputs the total energy (integrated value) of the radiation incident on the detection unit for every certain time period (1 frame) as detection data (measurement information). For example, the radiation detection apparatus 104 includes multiple detection units (detection elements) that are arranged in a two-dimensional shape. A flat panel-detector (FPD), which is constituted by a semiconductor material and in which multiple detection elements are arranged side by side in a grid shape can be used as the configuration of the radiation detection apparatus 104, and a configuration such as a line sensor can also be used thereas. It is also possible to include only one detection unit (detection element).

The radiation detection apparatus 104 uses the detection units (detection elements) to detect the intensities (energies) of the radiation that was output from the radiation generating apparatus 101 and has transmitted through the object 102. Although the object 102 is a living body in the present embodiment, it is also possible to use an object that is not a living body, such as an industrial product. If the radiation detection apparatus 104 includes a configuration for a flat panel detector, the detection units (detection elements) are arrayed in two dimensions so as to form multiple rows and multiple columns, for example. The radiation detection apparatus 104 includes a drive unit that drives the multiple detection units in units of rows or in units of columns, and the control unit 106 controls the drive unit to cause the multiple detection units (detection elements) to sequentially output the detection data (measurement information) corresponding to the total energy (integrated value) of the incident radiation.

The information detected by the detection units of the radiation detection apparatus 104 is sent to the data processing unit 107 (image processing unit) of the information processing apparatus 116 and processed. The data processing unit 107 (image processing unit) includes a moment usage unit 108 (obtaining unit), a classification unit 109, and a reconstruction unit 110. The functions of the units of the control unit 106 and the data processing unit 107 are configured using a program read from a CPU, a GPU, or a memory (not shown), for example. The configurations of the units of the control unit 106 and the data processing unit 107 may be constituted by an integrated circuit, as long as similar functions are achieved.

Figure 2:
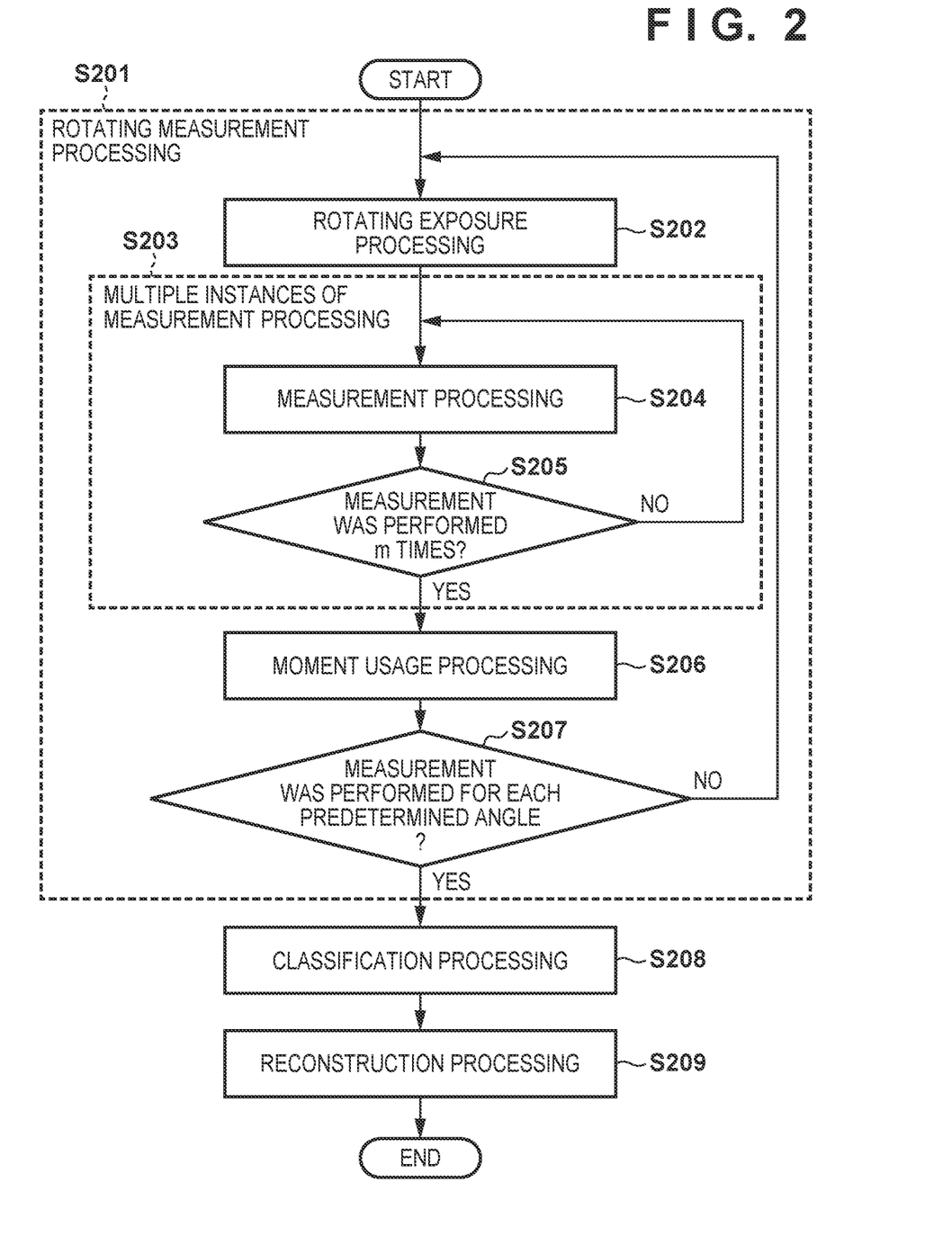
FIG. 2 is a diagram illustrating a processing flow of a CT apparatus according to an embodiment.

FIG. 2 is a diagram illustrating a flow of processing performed by the CT apparatus 100. The operations performed by the units of the control unit 106 and the data processing unit 107 shown in FIG. 1 to calculate the densities and the volume ratios of the substances constituting the object (constituent substances) will be described with reference to FIG. 2.

Rotating Measurement Processing: Step S201

First, in step S201, the control unit 106 executes rotating measurement processing. The rotating measurement processing has four steps (steps S202, S203, S206, S207).

Rotating Exposure Processing: Step S202

In step S202, the control unit 106 controls the rotating exposure unit 105 to rotate the radiation generating apparatus 101 and the radiation detection apparatus 104 centered about the object 102 to a predetermined rotation angle, and cause radiation to be emitted from the radiation generating apparatus 101.

Multiple Instances of Measurement Processing: Step S203

Next, in step S203, the control unit 106 executes multiple instances of measurement processing. The control unit 106 causes the radiation generating apparatus 101 and the radiation detection apparatus 104 to operate in conjunction with each other so as to execute the multiple instances of measurement processing. The multiple instances of measurement processing include two steps (steps S204 and S205). First, measurement is performed in step S204. The control unit 106 controls the radiation generating apparatus 101 so as to irradiate radiation at a constant tube voltage, and causes the detection results of the radiation incident on the detection units (detection elements) of the radiation detection apparatus 104 to be output each certain period. The measurement information measured by the detection units (detection elements) of the radiation detection apparatus 104 is denoted as $d_{p,i}(\xi)$. The affix p indicates information measured at a p-th rotation angle in the rotation measurement processing, and the affix i indicates information of the measurement executed for the i-th time. $\xi$ indicates the number of the detection unit (detection element). Next, in step S205, the control unit 106 determines whether or not a predetermined number of instances (m: an integer that is 2 or more) of measurement have ended. If the predetermined number of instances (m instances) of measurement have not ended (step S205—No), the processing is returned to step S204, and the measurement is performed once again. On the other hand, in the determination of step S205, if the predetermined number of instances (m instances) of measurement have ended (step S205—Yes), the processing is advanced to step S206. By executing the predetermined number of instances (m instances) of measurement, m instances' worth of measurement information is input to the moment usage unit 108.

Moment Usage Processing: Step S206

In step S206, the moment usage unit 108 (obtaining unit) obtains second measurement information of the radiation based on the moment of the measurement information obtained by detecting the radiation multiple times. That is, the moment usage unit 108 (obtaining unit) obtains the second measurement information of the radiation based on the moment of the measurement information $d_{pi}(\xi)$ measured in the multiple instances of measurement processing. The second measurement information includes information obtained using Equations 1 and 2 below, for example. For example, the moment usage unit 108 (obtaining unit) obtains, as the second measurement information, the photon count (<n>: average photon count) of the radiation incident on the detection unit based on the moment of the measurement information $d_{pi}(\xi)$ obtained by detecting the radiation multiple times. The moment usage unit 108 uses Equation 1 to obtain the average photon count $<n_p(\xi)>$ as the second measurement information.

$$E_{mean\,p}(\xi) = \frac{1}{\alpha(\xi)} \frac{\langle (d_p(\xi) - \langle d_p(\xi) \rangle)^2 \rangle}{\langle d_p(\xi) \rangle}, \quad \text{Equation 1}$$

$$\langle n_p(\xi) \rangle = \frac{\langle d_p(\xi) \rangle}{\alpha(\xi) E_{mean\,p}(\xi)}$$

Here, α is the conversion coefficient of the measurement information and the average energy, and $E_{mean\,p}(\xi)$ is the average energy. For example, the determination method of the conversion coefficient α is performed as follows. Based on the control performed by the control unit 106, first, the radiation emitted from a radiation source (radiation generating apparatus) having a known spectral distribution is measured such that only one photon is incident on a detection unit (detection element) by weakening the intensity of the radiation in a state with no object. This measurement is implemented multiple times, and the average of the measurement information is divided by the average energy of the spectral distribution, whereby conversion coefficient α can be obtained.

$<d_p(\xi)>$ is a first moment about the origin, and $<(d_p(\xi)-<d_p(\xi)>)^2>$ is a second central moment. The moment usage unit 108 (obtaining unit) can obtain the first moment about the origin ($<d_p(\xi)>$) and the second central moment $<(d_p(\xi)-<d_p(\xi)>)^2>$ through calculation using Equation 2 below.

$$\langle d_p(\xi) \rangle = \frac{1}{m} \sum_{i=1}^{m} d_{pi}(\xi), \quad \text{Equation 2}$$

$$\langle (d_p(\xi) - \langle d_p(\xi) \rangle)^2 \rangle = \frac{1}{m} \sum_{i=1}^{m} (d_{pi}(\xi) - \langle d_p(\xi) \rangle)^2$$

The reason why the average photon count $<n_p(\xi)>$ can be obtained using these equations will be described in detail below. In general, the photons incident on the detection units have a spectral distribution. If it is assumed that the spectral distribution can be approximated using the average energy $E_{mean\,p}(\xi)$, each piece of measurement information $d_{pi}(\xi)$ can be written as shown in Equation 3.

$$d_{pi}(\xi) = \alpha(\xi) E_{mean\,p}(\xi) n_{pi}(\xi) \quad \text{Equation 3}$$

In Equation 3, $n_{pi}(\xi)$ is the photon count. The photon count $n_{pi}(\xi)$ commonly has a fluctuation that follows a Poisson distribution, and it is known that in a Poisson distribution, the first moment about the origin and the second central moment are equal. That is, if the relationship between the first moment about the origin and the second central moment is expressed using the photon count $n_{pi}(\xi)$, Equation 4 below is achieved.

$$\langle n_p(\xi) \rangle = \langle (n_p(\xi) - \langle n_p(\xi) \rangle)^2 \rangle \quad \text{Equation 4}$$

If both sides of Equation 4 are multiplied by the square of $\alpha E_{mean\,p}(\xi)$ and adjustment is performed using Equation 3, Equations 1 and 2 can be obtained and the average photon count $<n_p(\xi)>$ can be obtained using Equations 1 and 2. Note that when the second central moment is to be obtained, the moment usage unit 108 may divide by m−1 instead of m (number of instances of measurement), that is, the moment usage unit 108 (obtaining unit) may obtain an unbiased variance.

Next, in step S207, the control unit 106 determines whether or not measurement at each predetermined angle has ended. If the measurement at each predetermined angle has not ended (step S207—No), the processing is returned to step S202 and the rotating exposure processing is executed. The control unit 106 controls the rotating exposure unit 105 to rotate the radiation generating apparatus 101 and the radiation detection apparatus 104 from the current rotation angle up to a further predetermined rotation angle, and causes the radiation to be emitted from the radiation generating apparatus 101.

On the other hand, if it is determined in step S207 that the measurement at each predetermined angle has ended (step S207—Yes), the processing is advanced to step S208. Note that the rotation angles at which imaging is executed can be set as appropriate. For example, angles obtained by evenly dividing a turn of 360° can be set as the predetermined angles. Also, in the present embodiment, the rotation angle of the radiation generating apparatus 101 and the radiation detection apparatus 104 is held in a state of having been rotated to a certain rotation angle, and thereafter the multiple instances of measurement processing are executed, but the gist of the present invention is not limited to this example. For example, it is also possible to use a method in which the radiation detection apparatus 104 performs multiple instances of measurement while the radiation generating apparatus 101 and the radiation detection apparatus 104 are rotated, and thereafter, the measurement information measured at adjacent rotation angles is collectively output, and moment usage processing is executed.

Classification Processing: Step S208

In step S208, the classification unit 109 classifies the object into a plurality of constituent substances. The classification unit 109 executes the classification processing to classify the substances constituting the object into at least two types of constituent substances. The classification unit 109 performs setting of the constituent substances to be classified, according to the underlying distribution of the constituent substance in the object that is to be obtained. The classification unit 109 performs classification into multiple types of constituent substances, such as iodine, which is a radiopaque dye, and soft tissue, soft tissue and bone, and the like, for example. The fact that the energy dependency of the linear attenuation coefficient or the mass attenuation coefficient differs for each constituent substance is used, and therefore constituent substances with different energy dependencies with respect to the energy of the radiation are selected. In the present embodiment, an example will be described in which the constituent substances constituting the object are classified into iodine and soft tissue. In the classification of the constituent substances performed by the classification unit 109, the object can be classified into multiple constituent substances based on operation input via an input unit, or an imaging condition or imaging location set from among a plurality of constituent substances stored in advance in a memory.

Reconstruction Processing: Step S209

In step S209, the reconstruction unit 110 executes reconstruction processing. Due to the execution of the reconstruction processing, the underlying distribution of the object (distribution of the constituent substances) is reconstructed. The reconstruction unit 110 reconstructs the information of the multiple constituent substances of the object based on the second measurement information. Also, the reconstruction unit 110 reconstructs the distribution of the constituent substances of the object based on the second measurement information. Here, the second measurement information is information that is obtained using Equations 1 and 2 in the case of the present embodiment.

In the present embodiment, the reconstruction unit 110 reconstructs the distribution of the constituent substances based on analysis of a function including the measurement information, the measurement information predicted based on the spectral distribution of the radiation and the constituent substances, the second measurement information, and the second measurement information predicted based on the spectral distribution of the radiation and the constituent substances. This function (target function f) is indicated by Equation 5 below. In Equation 5, the measurement information is information corresponding to $<d_p>$, the measurement information predicted based on the spectral distribution of the radiation and the constituent substances is information corresponding to $<d_p'>$, the second measurement information is information corresponding to $<n_p>$, and the second measurement information is predicted based on the spectral distribution of the radiation and the constituent substances is information corresponding to $<n_p'>$.

Also, in the present embodiment, the function in Equation 5 includes a difference (first difference) between the measurement information and the predicted measurement information, and a difference (second difference) between the second measurement information and the predicted measurement information. Through analysis of the function, the reconstruction unit 110 obtains information of the constituent substances according to which the first difference and the second difference are made as small as possible. Here, in Equation 5, the first difference corresponds to the term including $(<d_p>-<d_p'>)$, and in Equation 5, the second difference corresponds to the term including $(<n_p>-<n_p'>)$.

By analyzing Equation 5, the reconstruction unit 110 can obtain the densities or the volume ratios of the constituent substances corresponding to positions in the object as the information of the constituent substances. In the present embodiment, first, the densities of the constituent substances are used as the underlying distribution of the constituent substances to solve an optimization problem in which the densities are used as variables, whereby the underlying distribution of the constituent substances is reconstructed. The function f shown in Equation 5 is used as a target function, and the reconstruction unit 110 sets the densities as variables and obtains densities according to which the target function f is minimized. According to the result of the reconstruction processing performed by the reconstruction unit 110, the distribution of the densities of the constituent substances constituting the object can be estimated.

$$f = \frac{1}{2}\sum_{p,\xi} \{\langle n_p(\xi)\rangle - \langle n_p'(\xi)\rangle\}^2 + \frac{1}{2}\sum_{p,\xi} \{\langle d_p(\xi)\rangle - \langle d_p'(\xi)\rangle\}^2 \quad \text{Equation 5}$$

The reconstruction unit 110 reconstructs the distribution of the constituent substances based on the analysis of the function shown in Equation 5. In Equation 5, the second measurement information $<n_p'(\xi)>$ predicted based on the spectral distribution of the radiation and the constituent substances is defined by Equation 6, and the measurement information $<d_p'(\xi)>$ predicted based on the spectral distribution of the radiation and the constituent substances is defined by Equation 7.

$$\langle n_p'(\xi)\rangle = \int \langle S_p(\xi,E)\rangle \exp(-\int_{l_{p\xi}}\mu(r,E)dr)dE \quad \text{Equation 6}$$

$$\langle d_p'(\xi)\rangle = \alpha(\xi)\int \langle S_p(\xi,E)\rangle E\exp(-\int_{l_{p\xi}}\mu(r,E)dr)dE \quad \text{Equation 7}$$

In Equations 6 and 7, $<s_p(\xi,E)>$ is the spectral distribution of the radiation source. That is, $<s_p(\xi,E)>$ is the average value relating to the period of the number of photons that are irradiated to the ξ-th detection element at the time of the p-th rotation angle and have the energy E. The reconstruction unit 110 executes the integration calculation in the exponential functions in Equations 6 and 7 on the linear path from the radiation generating apparatus 101 to the ξ-th detection unit (detection element) at the time of the p-th rotation angle. Also, in Equations 6 and 7, μ(r,E) is the linear attenuation coefficient at position r in the object, corresponding to the energy E, and is defined by Equation 8 below. Here, the position r in the object is indicated by three-dimensional position information (three-dimensional coordinates).

$$\mu(r, E) = \sum_k \varphi_k(E)\rho_k(r) \quad \text{Equation 8}$$

In Equation 8, k indicates the k-th constituent substance constituting the object, $\varphi_k$ is a mass attenuation coefficient of the k-th constituent substance, and $\rho_k(r)$ is the density at the position r in the k-th constituent substance. In the present embodiment, in step S208 before, the classification unit 109 classified the object into iodine and soft tissue, and therefore Equation 8 is rewritten according to Equation 9 below.

$$\mu(r,E) = \varphi_{Iodine}(E)\rho_{Iodine}(r) + \varphi_{tissue}(E)\rho_{tissue}(r) \quad \text{Equation 9}$$

Accordingly, in the case of the present embodiment, the reconstruction unit 110 analyzes the optimization problem of Equation 5 using the relationships in Equations 6, 7, and 9. The reconstruction unit 110 can perform numerical analysis using the Gauss-Newton method, for example, as a solution method for the optimization problem. The function of Equation 5 includes the difference between the measurement information and the predicted measurement information, and the difference between the second measurement information and the predicted second measurement information, and based on the analysis, the reconstruction unit 110 obtains the information of the constituent substances according to which the differences decrease.

The setting of the target function f that is to be analyzed by the reconstruction unit 110 is not limited to being performed using Equation 5. For example, in the setting of the target function f, solution is performed by adding a priori knowledge relating to the regularizing terms and the density distribution according to need. For example, solution is performed by adding regularizing terms such as Tikhonov regularization or TV regularization to the target function f. Also, in another example, since it is unlikely that the density distribution inside of the object will locally fluctuate significantly, when the difference between densities at nearby locations is small, a function for reducing the value of the target function is added to the target function f, and thus the target function f can be set.

Also, in the target function f of Equation 5, the densities are used as variables in the underlying distribution constituting the object, but if the volume ratios are used in the underlying distribution, the reconstruction unit 110 can analyze the optimization problem for minimizing the target function f shown in Equation 5 with the volume ratios used as variables. At this time, the definition of the linear attenuation coefficient is performed using Equation 10 below, and not Equation 8.

$$\mu(r, E) = \sum_k \mu_k(E) c_k(r) \qquad \text{Equation 10}$$

In Equation 10, $\mu_k(E)$ is the linear attenuation coefficient at the energy E of the k-th constituent substance, and $c_k(r)$ is the volume ratio at the position r of the k-th constituent substance. In the determination of $\mu_k(E)$, setting can be performed using the mass attenuation coefficient and the general density of the constituent substance. In this case, the reconstruction unit 110 analyzes the optimization problem of Equation 5 using the relationships in Equations 6, 7, and 10. The reconstruction unit 110 obtains volume ratios for minimizing the target function f with the volume ratios used as variables. According to the result of the reconstruction processing performed by the reconstruction unit 110, the distribution of the volume ratios of the constituent substances constituting the object can be estimated.

The control unit 106 functions as a display control unit to display the analysis result of the reconstruction unit 110 on the display apparatus 111. The control unit 106 can display the information of the constituent substances and a cross-sectional image of the object in combination on the display apparatus 111. As the information of the constituent substances, the control unit 106 can display the distribution of the densities of the constituent substances or the distribution of the volume ratios of the constituent substances on the display apparatus 111. That is, the control unit 106 displays the underlying distribution (e.g., the distribution of the densities or the volume ratios) of the substances constituting the object, which was obtained by the reconstruction processing of the reconstruction unit 110, as a diagnostic image on the display apparatus 111.

Figure 3A:
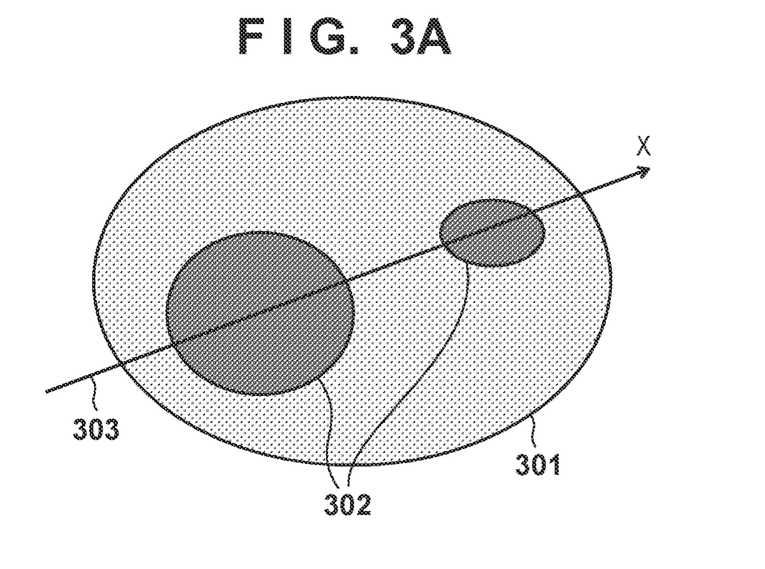
FIG. 3A is a diagram illustrating an imaging result.
Figure 3B:
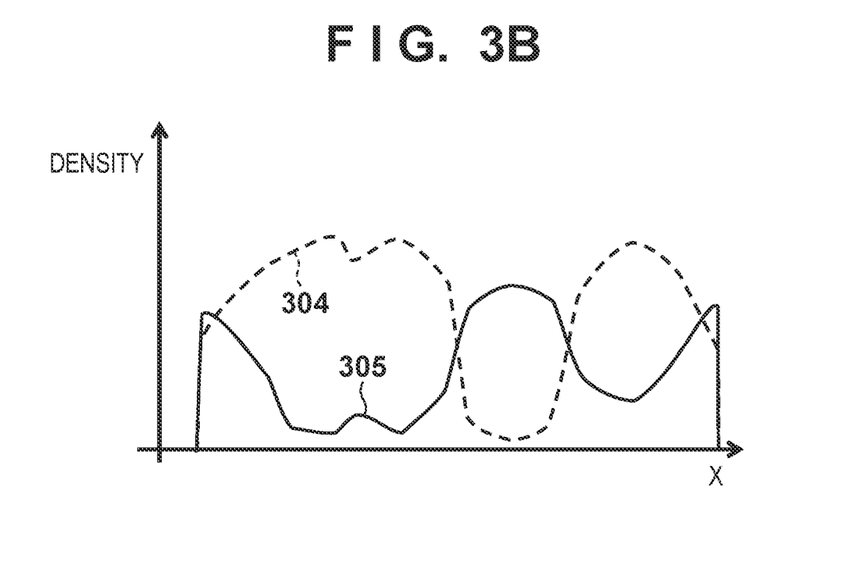
FIG. 3B is a diagram illustrating an imaging result.

FIGS. 3A and 3B are diagrams illustrating the result of imaging performed by the CT apparatus 100, FIG. 3A shows a cross-sectional image of a reconstructed object 301, and the differences in shading show the differences between the linear attenuation coefficients. A region 302 shows a region of the reconstructed object in which the linear attenuation coefficient is large. FIG. 3B shows a density distribution of a region on a straight line indicated by a straight line 303 of FIG. 3A. According to the embodiment of the present invention, the densities of the constituent substances constituting the object are determined, and therefore the distribution of the densities of the soft tissue indicated by a solid line 305 of FIG. 3B and the distribution of the densities of the iodine indicated by a broken line 304 can be determined, and the distribution of the densities or the volume ratios can be displayed in the image.

According to the present embodiment, the information of the constituent substances constituting the object can be obtained with high accuracy without being influenced by a decrease in the measurement accuracy. That is, measurement in which the tube voltage is changed is not performed, and the densities or the volume ratios of the multiple constituent substances constituting the object can be calculated using the energy of the radiation irradiated at a predetermined tube voltage. This is because, in addition to the measurement information $<d_p(\xi)>$ of the energy of the radiation, the second measurement information is obtained by the moment usage unit, and therefore the amount of information that can be used for estimation increases.

Also, in the present embodiment, $<n_p(\xi)>$ and $<d_p(\xi)>$ are defined by being divided by m for the purpose of the description, but it is also possible to use a value not divided by m, or in other words, it is also possible to use a sum instead of an average. Also, in the moment usage processing of the present embodiment, an example was shown in which processing is performed for each detection unit (detection element), but it is also possible to collectively process the measurement information of multiple detection units (detection elements) for which average energies and average photon counts that are approximately the same can be expected. In other words, it is also possible to perform processing for obtaining a sum by adding up the measurement information of the multiple detection units (detection elements) for which average energies and average photon counts that are about the same can be expected, as the target of obtaining the sum in Equation 2. The detection units (detection elements) for which average energies and average photon counts that are approximately the same can be expected are detection units that are arranged near each other among the multiple detection units (detection elements) that are arranged in a two-dimensional shape, for example. For this, for example, the control unit 106 compares the measurement information of a detection unit of interest and multiple peripheral detection units located in the periphery of the detection unit of interest, and the control unit 106 can add the processing of the multiple periphery detection units that output the measurement information for which the result of the comparison is within a predetermined threshold to the processing of the detection unit of interest in Equation 2 to obtain a sum. Note that the configuration of the present embodiment can also be used in a configuration in which dual energy imaging is performed on a subject using two types of radiation with different energies, and it is possible to further increase the energy count of the radiation (average energy count) by using the configuration of the present embodiment in the configuration for dual energy imaging as well.

Second Embodiment

In the second embodiment, processing of an object separation unit that separates space that is to be subjected to the reconstruction processing into an object and space around the object will be described. The space that is subjected to reconstruction processing includes an object 102 and air around the object 102 in some cases. In the first embodiment of the present invention, it was described that the object is classified into at least two types of constituent substances in the processing of the classification unit 109 (step S208), but in this case, it is necessary to separate (distinguish between) the object and the space around the object before the classification processing.

Figure 4:
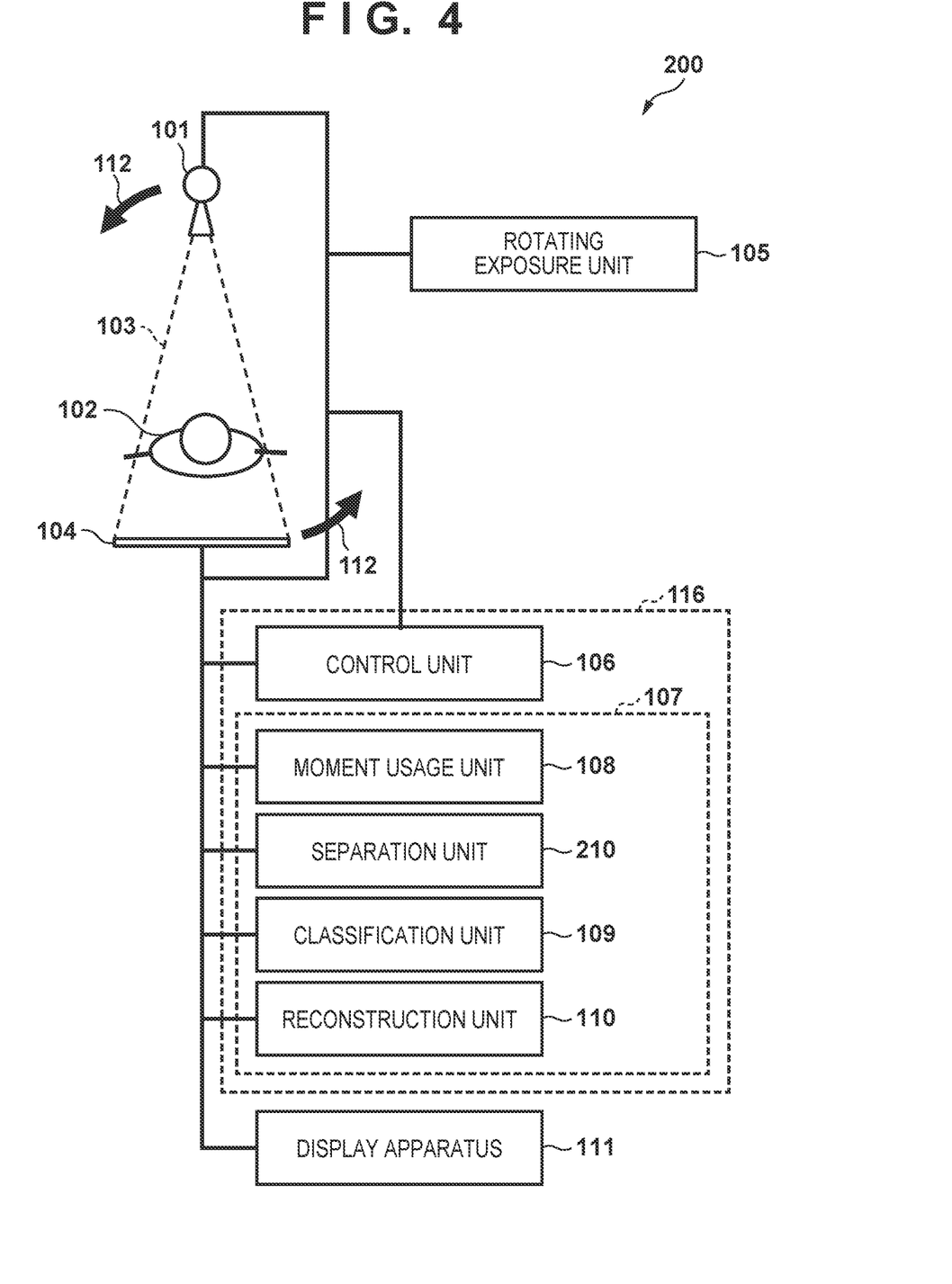
FIG. 4 is a diagram showing an exemplary configuration of a CT apparatus according to a second embodiment.
Figure 5:
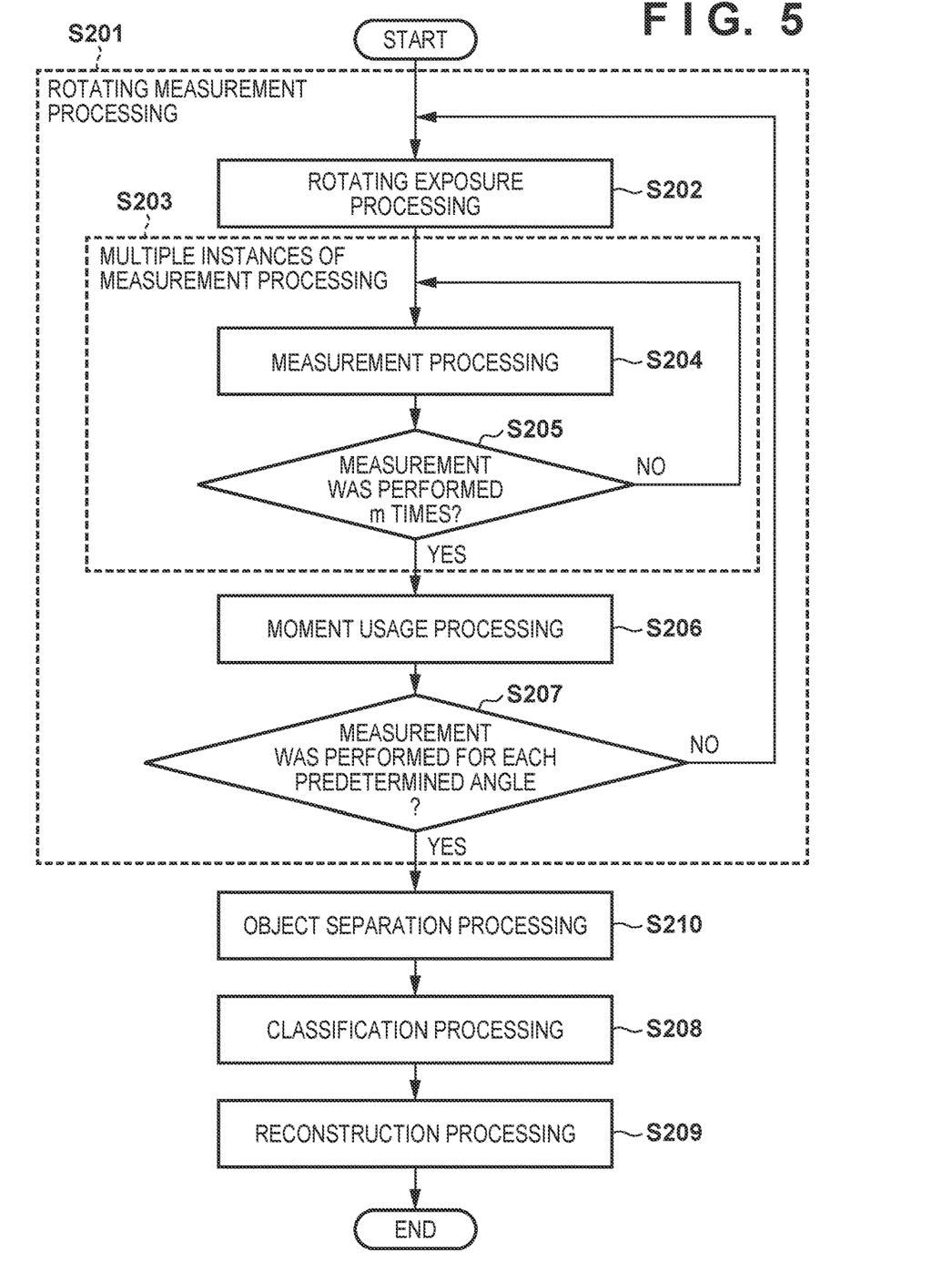
FIG. 5 is a diagram illustrating a processing flow of the CT apparatus according to the second embodiment.

FIG. 4 is a diagram showing an exemplary configuration of the CT apparatus 200 of the second embodiment. As shown in FIG. 4, the CT apparatus 200 includes a radiation generating apparatus 101, a radiation detection apparatus 104, a rotating exposure unit 105 that drives the radiation generating apparatus 101 and the radiation detection apparatus 104 so as to rotate in a state of opposing each other, and an information processing apparatus 116. The basic configuration is similar to that of the CT apparatus 100 of FIG. 1, but in the present embodiment, the configuration of the data processing unit 107 of the information processing apparatus 116 differs from the functional configuration of the CT apparatus 100 illustrated in FIG. 1 in that the object separation unit 210 (separation unit) is included. FIG. 5 is a diagram illustrating a flow of operations of the CT apparatus 200. In FIG. 5, the processing of steps S201 to S207 and steps S208 and S209 is similar to the processing of the steps of FIG. 2. In FIG. 5, the processing of steps S207 and S208 differs therefrom in that object separation processing (step S210) performed by the object separation unit 210 is added. The function of the object separation unit 210 (separation unit) is realized using a program read from a CPU, a GPU, or a memory (not shown), for example. The configuration of the object separation unit 210 may be constituted by an integrated circuit or the like, as long as similar functions are achieved.

The object separation unit 210 (separation unit) separates the object and the space around the object. The object separation unit 210 can separate the object and the space around the object based on the comparison of parameters obtained based on the reconstruction processing and the threshold. Examples of the parameters obtained based on the reconstruction processing include linear attenuation coefficients. Specifically, the object separation unit 210 reconstructs the attenuation coefficient of the space being subjected to reconstruction by using a sequential approximation reconstruction method, a filtered back projection (FBP) method, or the like, for example, based on the measurement information $<d_p(\xi)>$ measured by the detection unit (detection element). The living body that is the object and the air (space) around the object have different attenuation coefficients. For this reason, the object separation unit 210 separates the object 102 and the space around the object based on comparison of the attenuation coefficients obtained through the reconstruction processing and the threshold. Through this processing, it is possible to separate the object 102 from the space that is subjected to the reconstruction processing. In the present embodiment, in step S210, the classification processing of step S208 is executed on the object 102 that was separated from the space that is subjected to the reconstruction processing by the object separation unit 210.

According to the present embodiment, if something other than the object is included in the space that is subjected to the reconstruction processing, the classification processing is executed after the object is separated from the space subjected to the reconstruction processing.

According to the present invention, it is possible to reconstruct, with high accuracy, information on constituent substances of an object without being influenced by a decrease in measurement accuracy even if measurement in which a tube voltage is changed is not performed. For example, according to the CT apparatus of the present invention, it is possible to obtain, with high accuracy, the densities or volume ratios of substances constituting an object without being influenced by a decrease in measurement accuracy, even if measurement in which a tube voltage is changed is not performed.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A CT apparatus comprising:
    a detection unit configured to obtain measurement information based on a detection result of radiation irradiated based on a constant tube voltage;
    an obtaining unit configured to obtain second measurement information of the radiation based on a moment of the measurement information obtained by detecting the radiation a plurality of times;
    a classification unit configured to classify an object into a plurality of constituent substances; and
    a reconstruction unit configured to reconstruct information of the constituent substances of the object based on the second measurement information.

2. The CT apparatus according to claim 1, wherein based on the moment of the measurement information, the obtaining unit obtains, as the second measurement information, a photon count of the radiation incident on the detection unit.

3. The CT apparatus according to claim 1, wherein the reconstruction unit reconstructs a distribution of the constituent substances of the object based on the second measurement information.

4. The CT apparatus according to claim 1, wherein the reconstruction unit reconstructs the distribution of the constituent substances based on analysis of a function including the measurement information, measurement information predicted based on a spectral distribution of the radiation and the constituent substances, the second measurement information, and second measurement information predicted based on the spectral distribution of the radiation and the constituent substances.

5. The CT apparatus according to claim 4, wherein the function includes a difference between the measurement information and the predicted measurement information and a difference between the second measurement information and the predicted second measurement information, and based on the analysis, the reconstruction unit obtains information of the constituent substances according to which the differences decrease.

6. The CT apparatus according to claim 5, wherein the reconstruction unit obtains, as the information of the constituent substances, densities or volume ratios of the constituent substances corresponding to positions in the object.

7. The CT apparatus according to claim 1, further comprising
a display control unit configured to display an analysis result of the reconstruction unit on a display unit,
wherein the display control unit displays the information of the constituent substances and a cross-sectional image of the object in combination on the display unit.

8. The CT apparatus according to claim 7, wherein the display control unit displays, as the information of the constituent substances, a distribution of the densities of the constituent substances or a distribution of the volume ratios of the constituent substances on the display unit.

9. The CT apparatus according to claim 1, further comprising:
a rotating exposure unit configured to drive a radiation generating unit configured to irradiate radiation and the detection unit so as to rotate in a state of opposing each other; and
an imaging control unit configured to control operations of the radiation generating unit, the detection unit, and the rotating exposure unit,
wherein in a state in which the imaging control unit has controlled the rotating exposure unit so as to rotate the radiation generating unit and the detection unit by a predetermined angle,
the imaging control unit causes the radiation generating unit to irradiate the radiation based on a constant tube voltage, and
the imaging control unit controls the detection unit to output a plurality of detection results of the radiation incident on the detection unit each certain period.

10. The CT apparatus according to claim 1, further comprising
a separation unit configured to separate an object and space around the object,
wherein the separation unit separates the object and the space around the object based on comparison of parameters obtained based on the reconstruction processing and a threshold.

11. The CT apparatus according to claim 1, wherein the classification unit classifies the object into a plurality of constituent substances based on a set imaging condition or an imaging site.

12. The CT apparatus according to claim 1, wherein the obtaining unit is configured to obtain the second measurement information of the radiation based on a first moment about the origin and a second central moment by detecting the radiation a plurality of times.

13. A CT imaging method, comprising:
obtaining measurement information based on a detection result of radiation irradiated based on a constant tube voltage;
obtaining second measurement information of the radiation based on a moment of the measurement information obtained by detecting the radiation a plurality of times;
classifying an object into a plurality of constituent substances; and
reconstructing information of the constituent substances of the object based on the second measurement information.

14. A non-transitory computer-readable storage medium storing a program for causing a computer to execute the CT imaging method according to claim 13.

* * * * *